United States Patent

Drent et al.

Patent Number: 5,688,972
Date of Patent: Nov. 18, 1997

[54] PREPARATION OF ACETALS

[75] Inventors: Eit Drent; Dennis Humphrey Louis Pello, both of Amsterdam, Netherlands

[73] Assignee: Shell Oil Company, Houston, Tex.

[21] Appl. No.: 536,717

[22] Filed: Sep. 29, 1995

[30] Foreign Application Priority Data

Oct. 3, 1994 [EP] European Pat. Off. ............ 94202860

[51] Int. Cl.$^6$ .................. C07D 317/08; C07D 319/06; C07D 319/12

[52] U.S. Cl. ................ 549/369; 549/377; 549/430

[58] Field of Search ................... 549/430, 369, 549/377

[56] References Cited

FOREIGN PATENT DOCUMENTS 1127965  9/1968  United Kingdom .

*Primary Examiner*—Ba K. Trinh

[57] ABSTRACT

A process for the preparation of acetals by reacting one or more ethylenically unsaturated compounds with carbon monoxide, hydrogen and a liquid or dissolved organic nucleophilic compound containing at least two vicinal hydroxy groups in the presence of a catalyst system comprising:

a) a source of plantinum;
b) a source of anions; and
c) a bidentate ligand of the formula $$R^1R^2M^1RM^2R^3R^4 \qquad (I)$$

wherein $M^1$ and $M^2$ independently represent a phosphorus, arsenic or antimony atom, R represents a bivalent organic bridging group containing from 1 to 4 atoms in the bridge, $R^1$ and $R^2$ together represent a bivalent substituted or non-substituted cyclic group whereby the two free valencies are linked to $M^1$ and $R^3$ and $R^4$ independently represent a substituted or non-substituted hydrocarbyl group, or together represent a bivalent substituted or non-substituted cyclic group whereby the two free valencies are linked to $M^2$.

24 Claims, No Drawings

PREPARATION OF ACETALS

FIELD OF THE INVENTION

The invention relates to a process for the preparation of acetals by carbonylation of ethylenically unsaturated compounds.

BACKGROUND OF THE INVENTION

Acetals are interesting compounds which, in view of their reactivity, may be used as intermediates in the preparation of various commercially useful products, e.g. in the detergent field.

A known method for the preparation of acetals consists in an initial hydroformylation of olefins, whereby aldehydes and alcohols are formed, followed by a reaction between an aldehyde and an alcohol in a molar ratio of 1:2 to form an acetal and water.

In co-pending International patent application PCT/EP94/00894 a process is described for the carbonylation of acetylenically unsaturated compounds to produce unsaturated esters. The reaction is carried out in the presence of a nucleophilic compound having one or more removable hydrogen atoms. As catalyst use is made of a system based on a source of platinum, a bisphosphine ligand, preferably a 1,3-bis(diarylphosphino)propane, and a source of anions.

In two examples, relating to the preparation of butylacrylate by reacting acetylene, carbon monoxide and butanol, the formation of dibutylacetal as one of the by-products is mentioned. The catalyst applied in these experiments contained a bis(di(subst)ethylphosphino)propane ligand.

It has now been found that starting from olefins, using specific co-reactants and a catalyst system which, as regards the bidentate ligand, is based on a compound containing at least one bivalent cyclic group, acetals are produced in a single reaction step in good yield.

SUMMARY OF THE INVENTION

The invention therefore relates to a process for the preparation of acetals comprising reacting one or more ethylenically unsaturated compounds with carbon monoxide, hydrogen and a liquid or dissolved organic nucleophilic compound containing at least two vicinal hydroxy groups in the presence of a catalyst system comprising:

a) a source of platinum;

b) a source of anions; and c) a bidentate ligand of the formula

$$R^1R^2M^1RM^2R^3R^4 \qquad (I)$$

wherein $M^1$ and $M^2$ independently represent a phosphorus, arsenic or antimony atom, R represents a bivalent organic bridging group containing from 1 to 4 atoms in the bridge, $R^1$ and $R^2$ together represent a bivalent substituted or non-substituted cyclic group whereby the two free valencies are linked to $M^1$ and $R^3$ and $R^4$ independently represent a substituted or non-substituted hydrocarbyl group, or together represent a bivalent substituted or non-substituted cyclic group whereby the two free valencies are linked to $M^2$.

DESCRIPTION OF THE PREFERRED EMBODIMENTS

As ethylenically unsaturated compound, any compound containing at least one ethylenically unsaturated bond may be used. Preferably, olefins containing at least 4 carbon atoms are used, more preferably olefins having from 6 to 22 carbon atoms per molecule. Examples of suitable olefins are butene-1, hexene-1, hexene-2, pentene-1 and heptene-1.

If desired, compounds containing more than one double bond per molecule may be applied. Also, mixtures of ethylenically unsaturated compounds may be used. In view of the potential commercial outlets of the acetal products, a preferred category of starting materials consists in alpha-olefins having from 8 to 16 carbon atoms per molecule, e.g. octene-1, decene-1 and dodecene-1.

Although not wishing to be bound by a specific mechanism underlying the formation of acetals according to the invention, it is believed that, in the presence of the platinum containing catalyst system, carbon monoxide, a molecule of the organic nucleophilic compound and hydrogen react with the ethylenically unsaturated compound, forming a hydroxy-alkoxy alcohol which under ring closure and dehydration transforms into an acetal. The organic nucleophilic compounds containing at least two vicinal hydroxy groups include vicinal dihydroxy- and polyhydroxy compounds in which at least two hydroxy groups are in a vicinal position. Included are, inter alia, dihydric alcohols e.g. 1,2-diols and 2,3-diols such as 1,2-ethanediol, 1,2-propanediol, 1,2-butanediol, 2,3-butanediol and 1,2-pentanediol, trihydric alcohols such as glycerol and 1,2,4-cyclohexanetriol and polyhydric compounds such as 1,2,4,5-cyclohexanetetrol, ribose, glucose, methylglucose and lactose.

Preferably, di- or polyhydric alcohols are used having from 2 to 10 carbon atoms. In particular, recommended are commercially readily available compounds such as 1,2-ethanediol and glucose.

In the event the organic nucleophilic compound is neither liquid nor soluble in the one or more ethylenically unsaturated compounds, the process is carried out in the presence of a solvent as defined hereinafter wherein at least a significant amount of the organic nucleophilic compound is soluble.

The catalyst system of the invention, with regard to component a), is based on a source of platinum. As such, any platinum compound can be used which is capable of complexing with the atoms $M^1$ and $M^2$ in the bidentate ligand of formula (I).

Suitable platinum compounds include platinum(II) salt, such as sodium tetracyanoplatinate, potassium tetracyanoplatinate, platinum-bis(cyanobenzene)disulfate, potassium tetrachloroplatinate(II), platinum bis(triphenylphosphine)disulphate, potassium trichloro (ethylene)platinate(II) and potassium tetrachloroplatinate (II). Salts of platinum with carboxylic acids, in particular with carboxylic acids having up to 12 carbon atoms, e.g. acetic acid, are also suitable.

Preferably, as source of platinum use is made of organic platinum(II) complexes, platinum(II) acetylacetonate being in particular suitable.

As source of anions, component b) of the catalyst system, any compound generating these anions may be used. Sources of non-coordinating or substantially non-coordinating anions are preferred. In the context of the present specification this means that no, or very little, co-valent interaction occurs between the anion and the platinum in the catalyst.

Preferred anion sources are the acids, of which the anions are the conjugated base. Recommended are, in particular, acids having a pKa value of at most 4, measured at 18° C. in aqueous solution. Acids having a pKa value of at most 2, again measured at 18° C. in aqueous solution, are preferred.

Examples of suitable acids are mineral acids such as nitric acid, sulfuric acid, sulfonic acids such as methanesulfonic acid, tert-buthanesulfonic acid and p-toluenesulfonic acid, halomethanesulfonic acids, for example trifluoromethanesulfonic acid, chloromethanesulfonic acid and trichloromethanesulfonic acid and halogenated carboxylic acids, such as trifluoro- and trichloroacetic acid. Sulfonic acids are preferred.

Also recommended are complex anions such as the anions generated by a combination of a Lewis acid, such as $BF_3$, $AlCl_3$, $SnF_2$, $SnCl_2$, $Sn(CF_3SO_3)_2$ and $GeCl_2$ and a protic acid such as a sulfonic acid or a hydrohalogenic acid. Tin(II)chloride is a preferred Lewis acid to participate in the catalyst system. Examples of suitable complex anion-generating substances are $H(BF_4)$, $H[SnCl_2.CF_3SO_3]$, $H(SnCl_3)$ and $H(PF_6)$. In the bidentate ligands of the formula (I), constituting component c) of the catalyst system, $M^1$ and $M^2$ preferably each represent a phosphorus atom, in which case the bidentate ligand is a bisphosphine. The organic bridging group R preferably contains 2 atoms in the bridge. If both atoms in the bridge are carbon atoms, which is preferred, R advantageously represents an ethylene group.

The bivalent cyclic group, represented by $R^1$ together with $R^2$ preferably contains at least 5 ring atoms, typically from 6 to 9 carbon ring atoms. Favorable results are especially obtained, if in the bidentate ligand of formula (I) $R^1$ together with $R^2$ and $R^3$ together with $R^4$ represent a bivalent cyclic group with 8 or 9 carbon ring atoms in the cyclic group.

If desired, ligands may be used in which the bivalent cyclic groups contain one or two heteroatoms in the ring such as oxygen or nitrogen atoms.

The cyclic group(s), represented by $R^1$ together with $R^2$ and/or $R^3$ together with $R^4$, may contain substituents such as alkyl groups, in particular lower alkyl groups with 1 to 3 carbon atoms, for example methyl- or isopropyl groups, alkoxy groups or halogen atoms. However, in general the presence of substituents in the cyclic groups does not provide significant advantages and may sometimes complicate the preparation of the ligands.

For the preparation of the bidentate ligands of formula (I), known techniques may be used, for example, the preparation method disclosed in UK 1,127,965.

$R^3$ and $R^4$ may independently represent various hydrocarbyl groups, optionally substituted with substituents such as alkoxy groups with 1–4 carbon atoms, halogen atoms or ($C_1$–$C_4$ alkyl) amino groups. However, preferably $R^3$ together with $R^4$ has the same meaning as $R^1$ together with $R^2$.

The amounts of components b) and c), relative to the amount of component a), may vary considerably. Advantageously, the amount of component b) is selected such that per gram atom of platinum from 0.5 to 15, in particular from 1 to 8 anion equivalents are present.

The molar amount of bidentate ligand of formula (I) is preferably selected such that per gram atom of platinum from 0.5 to 10, in particular from 1 to 6 moles of bidentate ligand are present.

The quantity of catalyst system used in the process of the invention is usually in the range of $10^{-8}$ to $10^{-1}$ gram atoms of platinum per molecule of ethylenically unsaturated compound, preferably in the range of $10^{-7}$ to $10^{-2}$ on the same basis.

The process of the invention is preferably performed in the presence of a solvent in which the ethylenically unsaturated compound, the catalyst and for practical purposes at least a significant amount of the nucleophilic compound containing at least two vicinal hydroxy groups are soluble. In some cases, an excess of the (liquid) nucleophilic compound may be used, part of which serves as the reaction solvent. In general, the use of an inert solvent is preferred. As such, aprotic liquids containing a polar group are in particular recommended. Very suitable solvents are cyclic and non-cyclic ethers such as dimethylether, diethylether, methylethylether, anisole, 2,5,8-trioxanonane (diglyme) and sulfones such as diethylsulfone, dimethylsulfone, sulfolane (tetrahydrothiophene-2,2-dioxide), 2-methylsulfolane and sulfolene. Sulfolane represents a particularly preferred solvent. Mixtures of solvents may also be used, if so desired, e.g. a mixture of sulfolane and diglyme.

The process of the invention is conveniently carried out at moderate reaction temperatures and pressures. Suitable reaction temperatures are usually in the range of 40° to 200° C., temperatures in the range of 50° to 150° C. and in particular in the range of 60° to 130° C. being preferred.

The total reaction pressure is preferably in the range of 10 to 100 bar, pressures outside this range not being precluded. The total reaction pressure is substantially equal to the sum of the partial pressures of hydrogen and carbon monoxide. The molar ratio between hydrogen and carbon monoxide may vary, but preferably this ratio is selected in the range of 1:3 to 3:1. Small amounts of inert gases, contributing to the total pressure, may also be present.

The invention will be illustrated by the following non-limiting examples.

EXAMPLE 1

A 250 ml magnetically stirred "Hastelloy C" (Hastelloy is a trade mark) autoclave was charged with 20 ml of 1-octene, 30 ml of 1,2-ethanediol, 0.25 mmol of platinum(II)(acetylacetonate)$_2$, 0.6 mmol of 1,2-bis(cyclooctylenephosphino)ethane, 0.5 mmol of trifluoromethanesulfonic acid and 0.5 mmol of tin(II)chloride.

After being flushed, the autoclave was pressurized with carbon monoxide and hydrogen to a partial pressure of 30 bar of each and subsequently sealed.

The contents were heated to a temperature of 102° C. and maintained at that temperature until the reaction was virtually complete.

The pressure drop was measured and subsequently the reaction mixture was cooled to ambient temperature. The product was analyzed by Gas Liquid Chromatography. The conversion, the amount of formed acetal as percentage of converted olefin and the rate, expressed as moles of product per gram atom of platinum and per hour, are shown in Table 1.

EXAMPLE 2

An experiment was carried out, substantially as described in Example 1 with the following differences:
  i) the amount of 1-octene was 10 ml, instead of 20 ml;
  ii) as co-reactant 18 g of glucose was used, instead of 1,2-ethanediol. Additionally, 100 ml of diglyme was used as solvent; and
  iii) the reaction temperature was 88° C., instead of 102° C.

Further details and analytical results are shown in Table 1.

EXAMPLE 3

An experiment was carried out, substantially as described in Example 2, with the difference that 100 ml of sulfolane was used as solvent, instead of diglyme.

Further details and analytical results are shown in Table 1.

Example A (for comparison, not according to the invention)

An experiment was carried out, substantially as described in Example 2, with the following differences.

i) the amount of 1-octene was 15 ml, instead of 10 ml;

ii) 0.5 mmol of p-toluenesulfonic acid was used, instead of trifluoromethanesulfonic acid; and iii) 100 ml of toluene was used as solvent, instead of diglyme.

It was observed that glucose had not dissolved during the reaction. Analysis of the reaction product showed that only aldehyde (a hydroformylation product) had been formed.

Further details and analytical results are given in Table 1.

EXAMPLE 4

An experiment was carried out, substantially as described in Example 3, with the following differences:

i) 30 ml of 1-tetradecene was used, instead of 1-octene;

ii) 20 g of 1-D-methylglucose was used, instead of glucose; and iii) the reaction temperature was 84° C., instead of 88° C.

Further details and analytical results are given in Table 1.

EXAMPLE 5

An experiment was carried out, substantially as described in Example 3, with the following differences:

i) 20 ml of 1-tetradecene was used, instead of 1-octene; and ii) the reaction temperature was 89° C., instead of 88° C.

Further details and analytical results are given in Table 1.

TABLE 1

| Ex. No. | Temp. (°C.) | Total reaction time (h) | Olefin conversion (%) | Acetal formation (%) | Rate mol/gat/hr |
|---|---|---|---|---|---|
| 1 | 102 | 10 | 90 (after 3h) | >90 | 150 |
| 2 | 88 | 12 | >95 | >90 | 90 |
| 3 | 88 | 12 | >95 | >90 | 60 |
| A | 88 | 10 | >95 | — | n.d. |
| 4 | 84 | 15 | 40 | 50 | 30 |
| 5 | 89 | 15 | 100 | 100 | 30 |

What is claimed is:

1. A process for the preparation of acetals which comprises reacting one or more ethylenically unsaturated compounds with carbon monoxide, hydrogen and a liquid or dissolved organic nucleophilic compound containing at least two vicinal hydroxy groups in the presence of a catalyst system comprising:

a) a source of platinum;

b) a source of anions; and c) a bidentate ligand of the formula

$$R^1R^2M^1RM^2R^3R^4 \quad (I)$$

wherein $M^1$ and $M^2$ independently represent a phosphorus, arsenic or antimony atom, R represents a bivalent organic bridging group containing from 1 to 4 atoms in the bridge, $R^1$ and $R^2$ together represent a bivalent substituted or non-substituted cyclic group wherein the two free valencies are linked to $M^1$, and $R^3$ and $R^4$ independently represent a substituted or non-substituted hydrocarbyl group, or together represent a bivalent substituted or non-substituted cyclic group wherein the two free valencies are linked to $M^2$.

2. The process as claimed in claim 1, wherein said ethylenically unsaturated compound is an olefin having at least 4 carbon atoms.

3. The process as claimed in claim 1, wherein said ethylenically unsaturated compound is an olefin having from 6 to 22 carbon atoms.

4. The process as claimed in claim 1, wherein said ethylenically unsaturated compound comprises one or more alpha-olefins having from 8 to 16 carbon atoms are used.

5. The process as claimed in claim 1, wherein the organic nucleophilic compound is an alcohol selected from the group consisting of a di- alcohol having from 2 to 10 carbon atoms and a polyhydric alcohol having from 2 to 10 carbon atoms.

6. The process as claimed in claim 5, wherein the nucleophilic compound is 1,2-ethanediol.

7. The process as claimed in claim 5, wherein the nucleophilic compound is glucose.

8. The process as claimed in claim 1, wherein said source of platinum is a platinum compound.

9. The process as claimed in claim 8, wherein said platinum compound is platinum(II)acetylacetonate.

10. The process as claimed in claim 1, wherein said source of anions is an acid having a pKa no more than about 4.

11. The process as claimed in claim 10, wherein said source of anions is an acid having a pKa no more than about 2.

12. The process as claimed in claim 10, wherein said source of anions is a sulfonic acid.

13. The process as claimed in claim 10, wherein said source of anions comprises is a combination of a Lewis acid and a protic acid.

14. The process as claimed in claim 13, wherein the Lewis acid is tin(II)chloride.

15. The process as claimed in claim 1, wherein in said bidentate ligand of formula (I), $M^1$ and $M^2$ each represent a phosphorus atom.

16. The process as claimed in claim 1, wherein in said bidentate ligand of formula (I), R represents an ethylene group.

17. The process as claimed in claim 1, wherein in said bidentate ligand of formula (I), $R^1$ together with $R^2$, represents a substituted or non-substituted bivalent cyclic group with at least 5 ring atoms in the cyclic group.

18. The process as claimed in claim 17, wherein in the bidentate ligand of formula (I), $R^1$ together with $R^2$ and $R^3$ together with $R^4$ represent a bivalent cyclic group with 8 or 9 carbon ring atoms in the cyclic group.

19. The process as claimed in claim 15, wherein the bidentate ligand of formula (I) is 1,2-bis(cyclooctylenephosphino)ethane.

20. The process as claimed in claim 1, wherein the reaction is carried out in the presence of a solvent.

21. The process as claimed in claim 20, wherein said solvent is a polar aprotic liquid.

22. The process as claimed in claim 1, wherein the reaction is carried out at a temperature in the range of from about 50° to about 150° C.

23. The process as claimed in claim 1, wherein the molar ratio between of carbon monoxide to hydrogen is in the range of from about 1:3 to about 3:1.

24. The process as claimed in claim 1, wherein the reaction is carried out at a total pressure in the range of from about 10 to about 100 bar.

* * * * *